United States Patent [19]
Obersat

[11] Patent Number: 5,275,560
[45] Date of Patent: Jan. 4, 1994

[54] REPLACEABLE FRICTION ELEMENT FOR DENTAL PROSTHESIS

[76] Inventor: Adam Obersat, Logenstr. 4, 6750 Kaiserslautern/Pfalz, Fed. Rep. of Germany

[21] Appl. No.: 846,555

[22] Filed: Mar. 5, 1992

[30] Foreign Application Priority Data

Mar. 13, 1991 [DE] Fed. Rep. of Germany ........... 91 03022[U]

[51] Int. Cl.$^5$ .................... A61C 13/12; A61C 13/225
[52] U.S. Cl. ..................................... 433/177; 433/172
[58] Field of Search .............................. 433/172, 177

[56] References Cited

U.S. PATENT DOCUMENTS

| | | | |
|---|---|---|---|
| 1,719,314 | 9/1926 | Stern | 433/177 |
| 3,380,161 | 4/1968 | Weissman | 433/177 |
| 3,990,150 | 11/1976 | Giovannini | 433/177 |
| 4,348,181 | 9/1982 | Dawson | 433/172 |
| 4,488,875 | 12/1984 | Niznick | 433/173 |
| 4,518,357 | 5/1985 | Brinkmann et al. | 433/173 |
| 4,957,438 | 9/1990 | Bax | 433/180 |

FOREIGN PATENT DOCUMENTS 0136671 1/1988 European Pat. Off. .

Primary Examiner—John J. Wilson
Assistant Examiner—Cindy A. Cherichetti
Attorney, Agent, or Firm—Ostrolenk, Faber, Gerb & Soffen

[57] ABSTRACT

A friction element particularly for anchoring one removable telescopable part of a dental prosthesis on another. The one part has an opening through it in which the friction element is disposed. The friction element has a shank in the opening and has a friction head with a friction surface above the part and at one end of the opening. The friction element is of resilient plastic material. The friction head has a tapering, conical or convex bottom side and the opening in the one part is correspondingly shaped. The shank of the friction element has radial tabs which resiliently engage the inside of the opening. The shank may be of a length and the opening may be so shaped that one friction tab is behind the opening and engages the other side of the one part for preventing removal of the friction element. A detent recess in the other part receives the friction head on the telescoping of the parts together.

22 Claims, 3 Drawing Sheets

REPLACEABLE FRICTION ELEMENT FOR DENTAL PROSTHESIS

BACKGROUND OF THE INVENTION

The present invention relates to replaceable friction elements for use in frictional connection of separable and removable dental prostheses, which prostheses consist of male and female parts.

In dental prostheses, special connecting elements are used for anchoring a removable prosthesis part on the denture remaining in the jaw. There are distinctions among these holding or connecting elements, resilient connecting elements, hinge-like connecting elements and rigid connecting elements. The present invention refers to resilient and rigid connecting elements, in which the holding function between the male and the female parts is produced by means of friction, and possibly also additionally by means of a detent connection.

To permit the desired removal of the prosthesis, for instance to clean it, without damaging the remaining denture, the friction between the male and female parts should not exceed a given amount. Detachment forces of between 300 and 500 grams are favorable. When the prosthesis is worn, the cooperating friction surfaces of the male and female parts become worn, their friction is lost, and the prosthesis becomes loose. There are a number of known solutions for remedying this, for instance, a so-called dovetail abutment with a replaceable metal bolt/spiral spring combination or a so-called snap lock with a metal ball/spiral spring combination. The spiral spring produces the pressure between the male and female parts which produces the holding force via the coefficients of friction of the parts. In addition, a detent recess can be worked into the surface opposite the ball or bolt so that the hold between the male and female parts is not only frictional but also by detents.

Another prefabricated friction element, which may also act as a detent, is known, for instance, from Federal Republic of Germany Publication A-33 35 904, which corresponds to European Patent Document No. 013667. That construction has an extremely short structural height because it uses a flat spring which is bent into an S-shape.

For use between telescopable parts, a so called TK snap is available. This is a prefabricated functional element with a resilient spherical friction surface. The spherical surface and spring are formed of a single sheet metal part which is shaped in a suitable manner and which is inserted into an undercut depression of suitable size.

One big problem in dental prosthesis is the small amount of space available for the connecting elements. All known connecting elements which have springs, regardless of whether they are spiral springs, flat springs or spring plates, require a substantial structural volume. Otherwise, the springs, which, as mentioned, produce frictional forces of 300 to 500 grams, become fatigued or break within a short period of time.

Another problem in connection with these connecting elements is oral hygiene. Saliva and traces of food enter the cavities which receive the springs, bolts and-/or balls. The contaminants cannot be removed upon the normal cleaning of the prosthesis because when the prosthesis has been removed, the opening is closed by the ball pin and/or spring element which produces the friction or detent.

SUMMARY OF THE INVENTION

It is an object of the present invention to provide a friction element of the aforementioned type for a prosthesis, which occupies only a slight volume, is readily replaceable and does not result in any problems with respect to oral hygiene.

One advantage of the friction element of the present invention is the drastic reduction of the volume occupied by the friction element because the head of the friction element, which effects the friction, and possibly also the detenting, is at the same time the spring. The shank of the friction element merely has the task of holding the friction element fast on its prosthesis part. The required length of the shank is extremely short. For an adhesive attachment, 1 mm, for instance, is sufficient.

Another essential advantage of the present invention is the considerable improvement in oral hygiene. With the prosthesis inserted, the head of the friction element is pressed strongly into a countersunk tapered wall entrance part, e.g., a cone, at the head end or entrance of the friction element holding opening. This hermetically seals off the denture from the penetration of saliva and food residue. The sealing effect is further supported by radially outwardly projecting elastic, resilient friction tabs located on the shank of the friction element. The tabs apply spring action against the interior wall of the friction element holding opening. Even if the holding opening is developed as a blind hole in the prosthesis part rather than a through hole completely through the prosthesis part, saliva and traces of food can be reliably excluded from penetrating and decomposing there.

Due to the small size and low cost of the friction element, which is made of plastic, it can be employed in practically any desired quantity and in practically any place. It is advisable to provide three or even more friction elements since, in that case, a statically determined support between the male and female parts is possible and metal to metal rubbing is eliminated upon the insertion and removal of the prosthesis.

The friction surface of the head of the friction element can, in principle, be developed in any desired manner. It can therefore be flat. In a preferred embodiment of the invention, the friction surface projects outward, e.g. it is generally rounded, particularly if a cooperating detent depression is provided in the wall of the other prosthesis part which is opposite the friction head when the prosthesis is assembled on the denture.

The shank preferably has elastic friction tabs which press resiliently against the wall of the holding opening. Advantageous cross-sectional shapes for the friction tabs are saw-tooth shape, undulated, or thread shapes. These cross-sectional shapes facilitate the insertion of the friction element and prevent its falling out of the opening.

The friction tabs permit additional anchoring of the friction element in the holding opening. For this purpose, the holding opening is countersunk in a cylindrical or frustoconical shape at the rear end. If the shank of the friction element is sufficiently long, at least the last friction tab will spread open in the countersink. The friction element is then seated fast in the opening and its accidental loss is prevented. In the event that a repair or replacement of the friction element is needed, it can nevertheless easily be removed by the dental technician and it can be replaced by a new friction element.

In another feature, the friction element may have a retaining head of plastic, which is placed on the shank from the rear. That retaining head is detent connected with the friction tabs. If the holding opening is conically countersunk on its rear side, then, in case of tensile stressing of the friction element, the retaining head is pressed against the shank or its friction tabs.

In the simplest case, the cross sections of the friction element and the holding opening for it are circular. However, it is possible to make those cross sections oval or rectangular without their functions suffering. If their cross sections are rectangular, there is the further possibility of cutting the friction element and possibly the additional holding head from a continuous extruded plastic part. This makes a substantial saving in expense possible.

For providing round and oval cross sections, the friction element and the holding head are preferably injection moldings. Injection moldings can be manufactured completely automatically in large numbers and at low cost. Production of them as machined parts is also possible.

Forming a bore hole or slot in the shank of the friction element softens the spring properties of the shank and possibly of the friction element as a whole.

In practice the friction element has a diameter of, for instance, 1 mm and a length of, for instance, 3 mm, while the retaining head has even smaller dimensions. In order to facilitate handling of the friction element and of the retaining head, it is advisable to form on a holder on either or both of them, in particular via an intended place of breakage between the holder and the element to which it is connected.

Other objects, features and advantages of the present invention are described with reference to the following description of the invention which refers to the accompanying drawings.

DETAILED DESCRIPTION OF THE INVENTION

Figure 1:
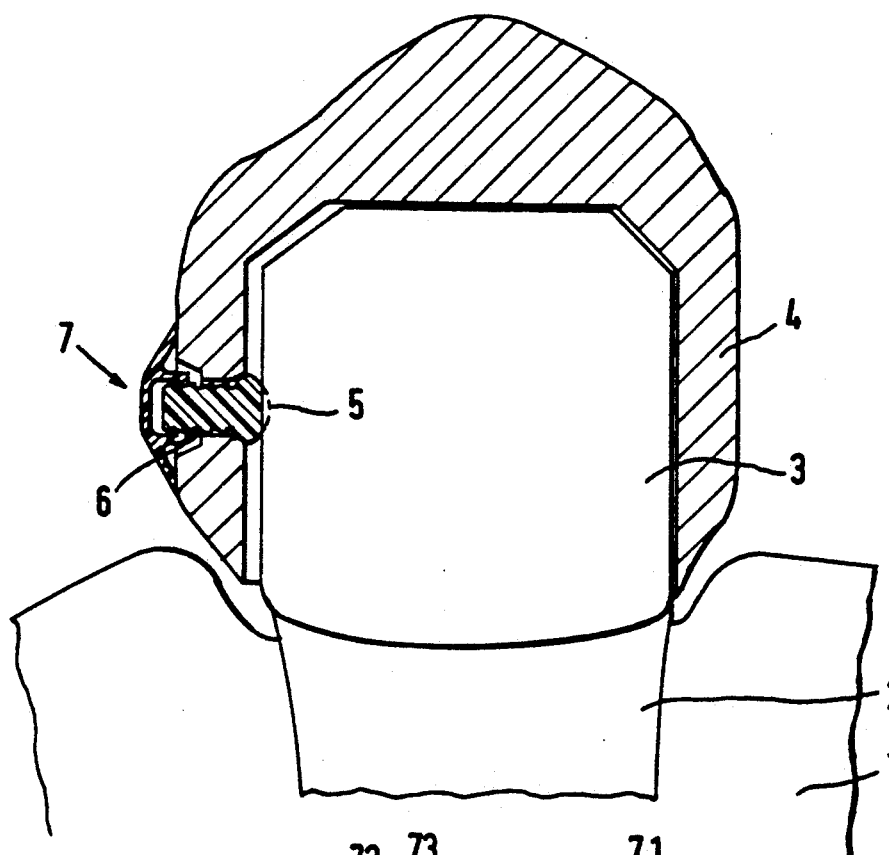
FIG. 1 is a section through a double crown including a friction element of the invention.

FIG. 1 is a cross section showing a jaw model 1, the casting of a tooth stump 2, a primary crown placed on the stump as a male part 3, and a secondary crown placed over the male part as a female part 4. The male part 3 and the female part 4 form a double crown, i.e. a closed telescopable assembly with cooperating opposing walls which are parallel.

One wall of the female part 4 has a hole 6 in it into which a friction element 7 comprised of plastic is inserted. The form and function of the friction element 7 is explained below based on FIGS. 2 to 8.

In that wall of the male part 3 which is opposite the friction element 7, there is a detent recess 5 in which the head of the friction element 7 engages, so that the holding action between the male part 3 and the female part 4 is not only frictional but, in addition, also detented.

It is obvious that the friction element 7 of the invention can be used in other applications than in the telescopable crowns of the type shown in FIG. 1. It can be used in all rigid and resilient connecting elements of dental prosthesis, because the extremely small structural volume of the friction element 7 and its low price permit considerably broader use than would be possible with friction elements of the prior art.

Figure 7:
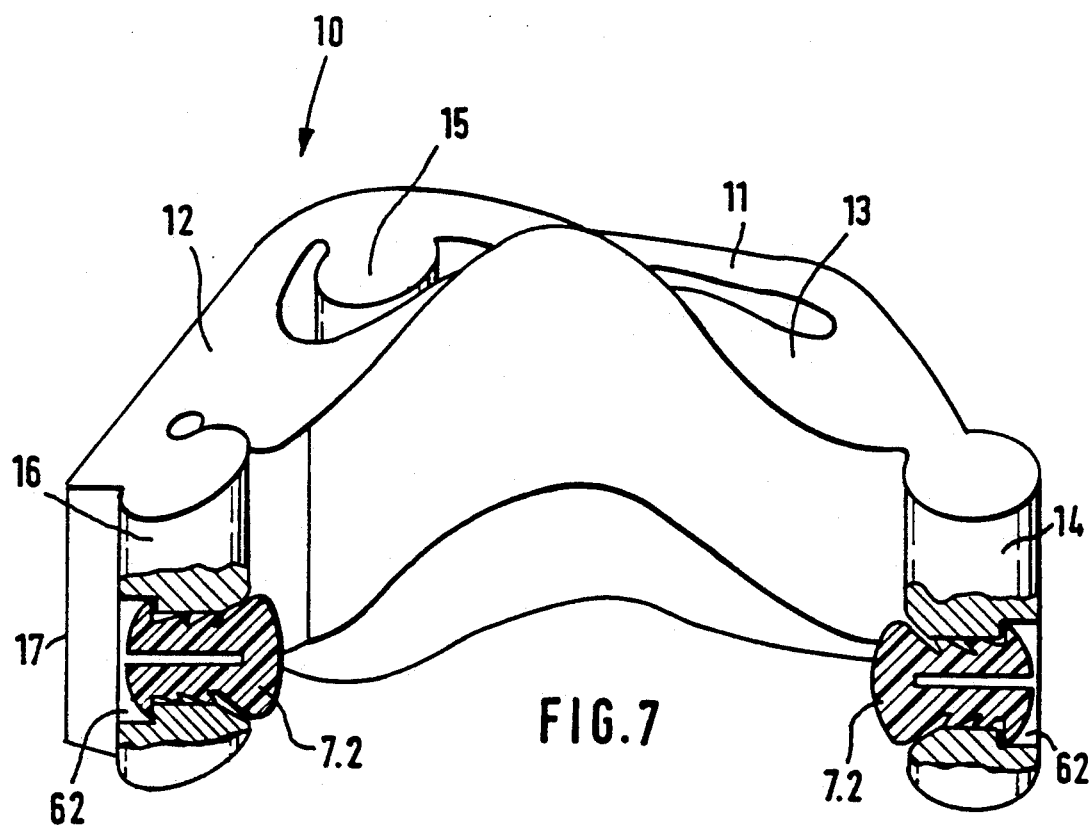
FIG. 7 is a perspective view, partially broken away, of a friction element installed in a telescopable part of a dental prosthesis.

One example in FIG. 7 shows the secondary part of a removable prosthesis in the form of a partial telescopable prosthesis part 10 with parallel walls, as described in Federal Republic of Germany Utility Model 91 02 106, which corresponds to U.S. application Ser. No. 07/839,251, filed Feb. 20, 1992. The part 10 comprises a lingual outer telescoping wall 11, a supporting telescoping wall 12, a female web part 13, and three friction enhancing partial cylinders 14, 15 and 16. The removable prosthesis (not shown) is fastened to the flat outer surface 17 of the supporting telescoping wall 12. In each of the friction cylinders 14, 15, 16, holding opening 62 are developed into which friction elements 7.2 are inserted in a manner which prevents the elements from coming out. In this way, a statically determined support is produced between the male and female parts. Furthermore, there is no metal to metal rubbing upon the insertion and removal of the prosthesis.

Figure 2:
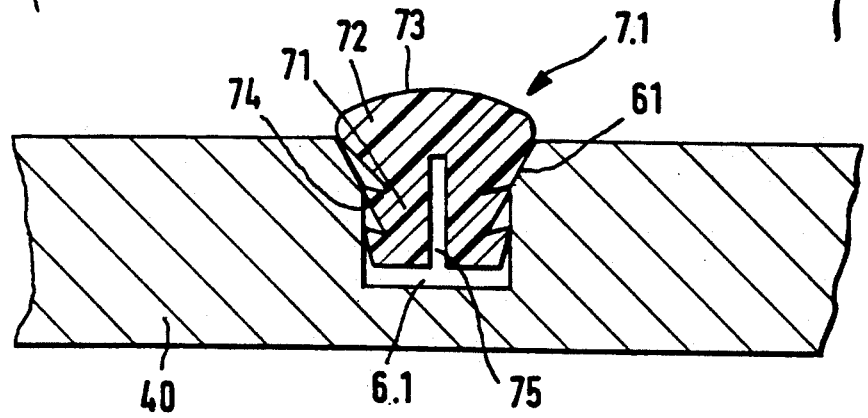
FIG. 2 is a section through a first embodiment of a friction element located in part of a supporting denture for a prosthesis.

FIG. 2 shows a cross section of a first, particularly simple friction element 7.1 which is inserted into a blind bore hole 6.1 in a wall 40 of a prosthesis part. The friction element 7.1 has a shank 71 which is provided with circumferential, radially outwardly projecting, elastic, friction tabs 74. The dimensions of these elements are selected so that the tabs apply themselves resiliently against the wall of the bore hole 6.1 and fix the friction element 7.1 there.

As an essential functional part, the friction element 7.1 has a friction head 72 with a bottom which is taperingly shaped, narrowing from the wider head to the narrower shank and a friction surface 73 which projects outward from the friction head 72. For example, the bottom of the head is of conical to outwardly convex in shape. The friction head 72 may be outwardly rounded. The adjacent end of the hole 6.1 in the wall 40 is conically countersunk at cone 61. Upon insertion of the prosthesis and the telescoping together of the prosthesis parts, the friction head is pressed into the cone 61. The necessary friction force is built up through the angle of the cone 61 in combination with the coefficient of friction and the elasticity of the plastic material, on the one hand, and the shape of the friction head 72, on the other hand.

If necessary, the friction and detenting forces can be reduced by the provision of a slit 75 or a bore extending into the friction element from the rear end.

Pressing the friction head 72 into the cone 61 hermetically seals off the hole 6.1 in the wall 40 from the penetration of saliva and food residue. Decomposition, which can cause bad breath, is therefore excluded.

In addition there is a possibility of replacing the friction element 7.1, for instance in the event of a needed repair, in a very simple manner without screwing, soldering, cutting, or the like. It can just as easily be subsequently added to traditional connection constructions, which in this way may again become functional.

Figure 3:
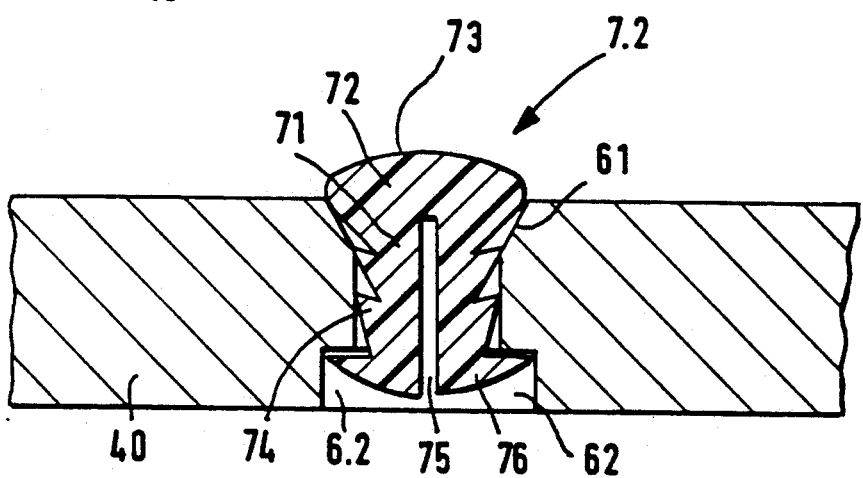
FIG. 3 is a section through a second embodiment of a friction element.

The end of the blind hole 6.1 can widen in a generally pear shape, like in FIG. 3, enabling anchoring of the friction element 7.1.

FIG. 3 shows another friction element 7.2. In this case, the opening 6 is developed as a continuous or through opening 6.2. The open rear end has a cylindrical countersink 62. The cross section of the countersink 62 enables the rearmost resilient friction element tab 76 to spread open so that the friction element 7.2 is seated nonremovably in the opening 6.2. Furthermore, the dental technician can easily replace the friction element 7.2 in the event a repair is needed.

With suitable development of the countersink 62 and the friction tabs 74, 76, sealing of the opening 6 against saliva and food residue from the rear side is also possible. However, there is a smaller residue problem here since with a continuous hole, as shown in FIG. 3, saliva and food residue can be removed substantially more easily than in the case of the blind hole in FIG. 2.

Figure 4:
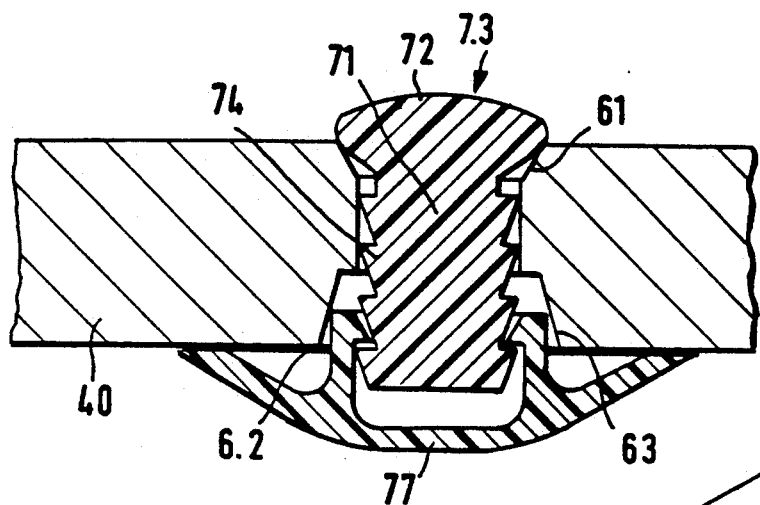
FIG. 4 is a section through a third embodiment of a friction element.

FIG. 4 shows a third friction element embodiment 7.3. On the rear of the wall 40 of the prosthesis part, an additional retaining head 77 is placed on the extended shank 71 of the friction element 7.3. The head 77 engages one of the friction tabs 74. In this embodiment, the tabs preferably have a saw-tooth cross section. Upon tensile stressing of the friction element 7.3, the shank of the retaining head 77 is pressed against the conical wall of the rear countersink 63 and is locked in position there. The continuous hole 6.2 has a frustoconical countersink 63, which facilitates the pushing in of the retaining head 77 and also makes possible the spreading apart of the rear friction tabs 74.

Figure 5:
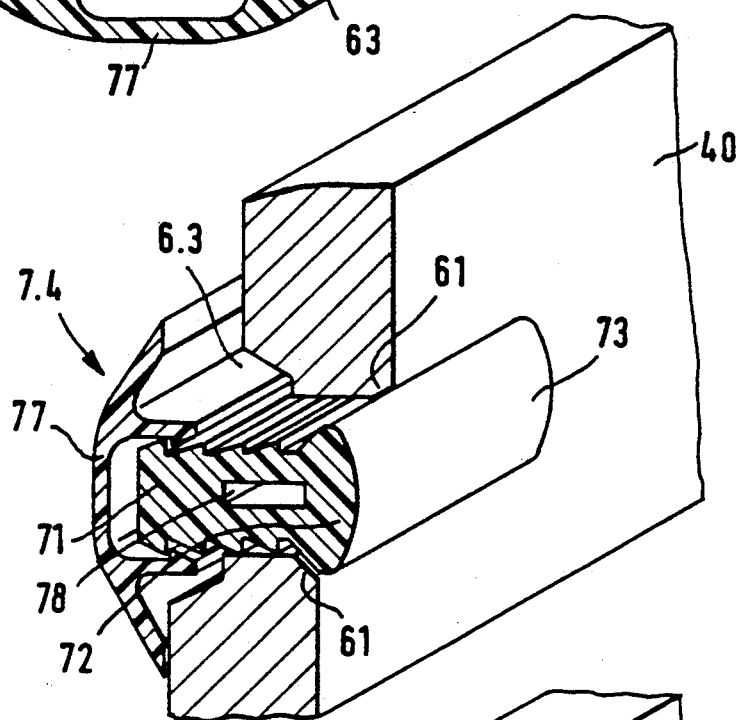
FIG. 5 is a section through a fourth embodiment of a friction element.
Figure 6:
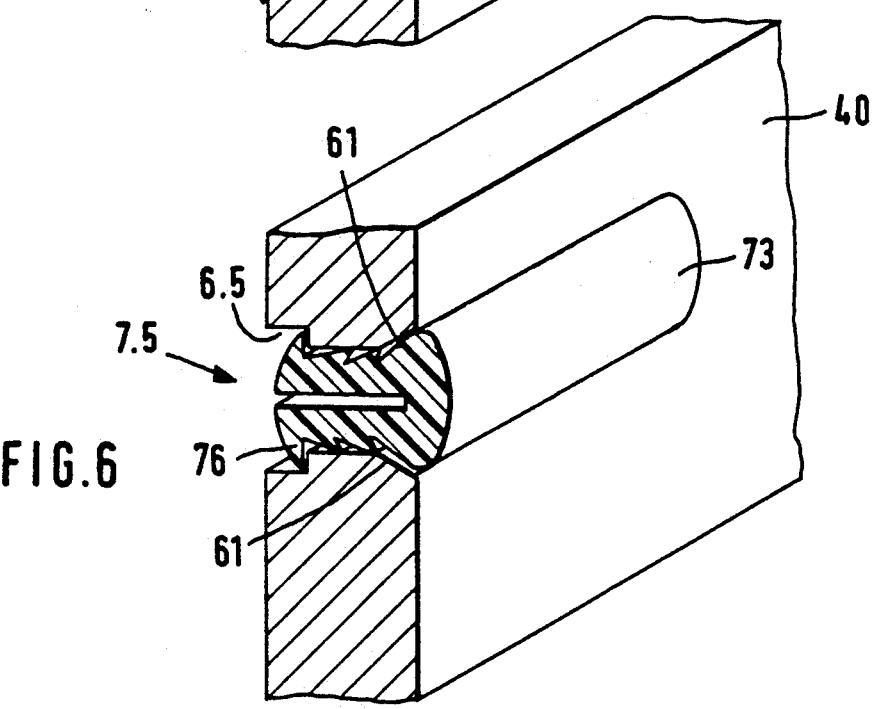
FIG. 6 is a section through a fifth embodiment of a friction element.

In the embodiments of FIGS. 2 to 4, the cross sections of the openings and the friction elements placed in them are circular. FIGS. 5 and 6 show that rectangular cross-sectional shapes are also available for the friction elements and the holes that receive them. Other shapes are also possible, for instance oval, cross-sectional shapes, but these are not shown separately. Other than the change from circular to generally rectangular cross-section, the construction and function of the friction element 7.4 in FIG. 5 corresponds to that of FIG. 4 while the construction and function of the friction element 7.5 in FIG. 6 corresponds to that of FIG. 3.

While the friction elements of FIGS. 2 to 4 must be produced individually by injection molding or machining, the friction elements shown in FIGS. 5 and 6 can be initially produced by a continuous extrusion and individual elements are then cut off. In this way, it is also possible to produce enclosed cavities or slots 78 inside the friction elements, as shown in FIG. 5 which, like the slit 75 in FIGS. 2 or 3, makes the element more flexible and squeezable which provides a more secure elastic holding in the hole.

Figure 8:
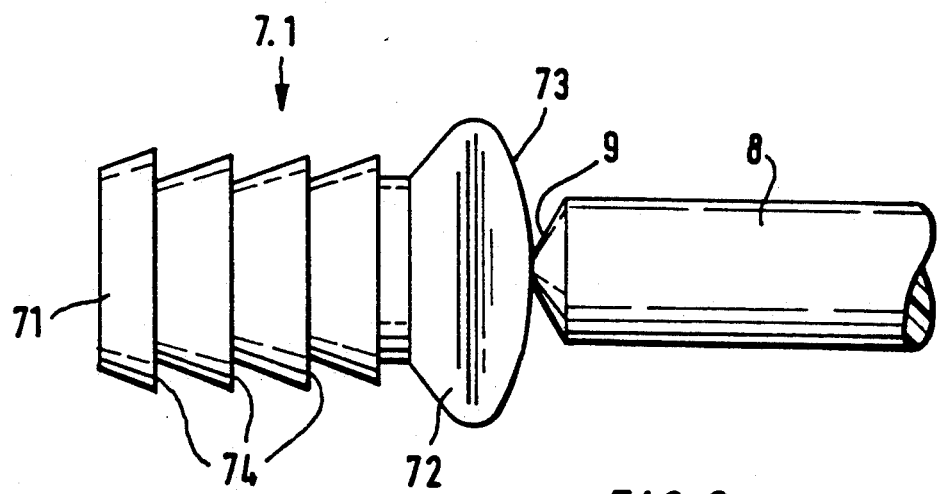
FIG. 8 is a friction element with a retainer formed on it.

FIG. 8 shows the friction element 7.1. On the outer friction surface 73 of the head 72, a holder 8 is formed on the end of the head 72 and is attached to it via a place of intended breakage 9. This holder makes it easier for a dental technician to handle the friction element, which is very small. The holder 8 can be adapted practically in any way desired to the existing circumstances. It may also be formed on a retaining head 77. After the mounting of the friction element, the holder 8 is broken off at the place of intended breakage 9.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A replaceable friction element made of an elastic material for emplacement in one of a male part and a female part of a dental prosthesis wherein the female part telescopes over the male part in a first direction, for frictionally holding the parts together;

the friction element comprising a shank, the shank having an end, a head on the end of the shank, the head having a friction surface outwardly away from the shank, the head having a bottom toward the shank, the bottom being generally taperingly shaped;

the one part having a holding opening in it extending transversely to said first direction, the opening being correspondingly shaped for slidingly receiving the shank in the opening, whereby the friction surface frictionally engages the other part of the dental prosthesis as the male and female parts telescope in said first direction, transversely with respect to said friction element;

the opening widening in the region adjacent the bottom of the head of the friction element, receiving the bottom of the head, whereby the bottom of the head is free to expand into said opening; and the angle of widening of the opening in the part toward the head being shaped so as to accommodate said head when compressed by engagement with the other part, as a function of the elasticity and coefficient of friction of the head and the shape of the head.

2. The friction element and the cooperating one part for receiving it of claim 1, wherein the friction element is comprised of an elastic plastic capable of friction contact with another part.

3. The friction element and the one part of claim 1, wherein the bottom of the head is generally conically shaped.

4. The friction element and the one part of claim 1, wherein the bottom of the head is generally outwardly convex shaped.

5. The friction element and the one part of claim 1, wherein the friction surface on the head is generally outwardly rounded.

6. The friction element and the one part of claim 1, wherein the friction surface on the head extends out from the surface of the one part.

7. The friction element and the one part of claim 1, further comprising a hole in the friction element shank.

8. The friction element and the one part of claim 1, further comprising friction tabs defined on and around the shank and shaped and sized to cooperate with the opening in the one part so that the tabs are deformed by the one part when the shank of the friction element is in the opening and the tabs rest resiliently against the wall of the opening.

9. The friction element and the one part of claim 8, wherein the tabs have a cross-section selected from the group consisting of saw tooth shape, undulating shape and thread shape.

10. The friction element and the one part of claim 8, wherein the one part is the female part, the opening in the one part has a rear end away from the end in which the bottom of the head of the friction element is disposed, the shank of the friction element being of such length and the rear end of the opening in the one part being located so that one of the friction tabs on the shank of the friction element resiliently and elastically spreads open in the space to the rear of the opening in the one part, and that friction tab would contact the rear of the one part preventing removal of the friction element from the opening in the one part.

11. The friction element and the one part of claim 8, wherein the respective cross-section of the friction element and the hole in the one part which receives the shank of the friction element is selected from the group consisting of round, oval and rectangular cross-sections.

12. The friction element and the one part of claim 8, wherein the one part is the female part; a retaining head exposed on the one part at the side of the one part away from the head of the friction element, the retaining head having an element which extends into the opening in the one part and engages one of the friction tabs of the shank of the friction element.

13. The friction element and the one part of claim 1, wherein the respective cross-section of the friction element and of the opening in the one part which receives the shank of the friction element is selected from the group consisting of round, oval and rectangular cross-sections.

14. The friction element and the one part of claim 1, wherein the one part is the female part; a retaining head at the side of the one part away from the head of the friction element, the retaining head having an element which extends into the opening in the one part and engages the shank of the friction element.

15. The friction element and the one part of claim 14, wherein the retaining head is an injection molded part.

16. The friction element and the one part of claim 1, wherein the friction element is cut from a continuously extruded piece.

17. The friction element and the one part of claim 1, wherein the friction element is an injection molded plastic element.

18. The friction element and the one part of claim 1, wherein the friction element is a lathe cut part.

19. The friction element and the one part of claim 1, further comprising a holder formed on and attached to the friction element at a place of intended separation where the holder is separable from the friction element.

20. The friction element and the one part of claim 19, wherein the holder is separably attached at the place of intended breakage to the head of the friction element.

21. The friction element and the one part of claim 1, further comprising the other of the male and female parts telescoping over and cooperating with the one part having the hole in which the friction element is disposed; the other part having a surface for engagement with the head of the friction element.

22. The friction element and both the one and the other parts of claim 21, further comprising a recess in the other part located opposite the head of the friction element and the head of the friction element being received in the recess for providing detented connection between the friction element and the one part with the other part.

* * * * *